(12) United States Patent
Hipp et al.

(10) Patent No.: US 11,307,924 B2
(45) Date of Patent: Apr. 19, 2022

(54) SEQUENCE MINING IN MEDICAL IOT DATA

(71) Applicant: Siemens Healthcare GmbH, Erlangen (DE)

(72) Inventors: Tobias Hipp, Nuremberg (DE); Thomas Hubauer, Garching bei Muenchen (DE); Ulli Waltinger, Neuburg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 53 days.

(21) Appl. No.: 16/819,939

(22) Filed: Mar. 16, 2020

(65) Prior Publication Data
US 2020/0310900 A1 Oct. 1, 2020

(30) Foreign Application Priority Data
Mar. 25, 2019 (EP) ..................................... 19164965

(51) Int. Cl.
*G06F 11/00* (2006.01)
*G06F 11/07* (2006.01)
(Continued)

(52) U.S. Cl.
CPC ........ *G06F 11/079* (2013.01); *G06F 11/0736* (2013.01); *G06F 11/0751* (2013.01);
(Continued)

(58) Field of Classification Search
CPC .. G06F 11/079; G06F 11/3006; G06F 11/036; G06F 11/0751; G06F 11/0778; G06N 20/00; G06N 5/04
See application file for complete search history.

(56) References Cited

U.S. PATENT DOCUMENTS 5,463,768 A * 10/1995 Cuddihy ............. G06F 11/2205
714/37
2010/0229239 A1* 9/2010 Rozenberg ............ G06F 21/552
726/24
(Continued)

OTHER PUBLICATIONS

Zaki, Mohammed J. "SPADE: An Efficient Algorithm for Mining Frequent Sequences" Machine Learning; vol. 42; pp. 31-60; 2001 // http://www.philippe-fournier-viger.com/spmf/SPADE.pdf.
(Continued)

*Primary Examiner* — Jonathan D Gibson
(74) *Attorney, Agent, or Firm* — Harness, Dickey & Pierce, P.L.C.

(57) ABSTRACT

A computer-implemented method for configuring a computing device for predictive maintenance, a computer-implemented method for predictive maintenance as well as a predictive maintenance apparatus are disclosed. Training log files including event sequences are examined iteratively for sequences of increasing length in order to determine a set of configuration data containing event sequences that have high predictive power for a system failure. Forward and backward gap values are defined such that not only sequences in the exact same temporal order as in the training log files are examined but also sequences with slightly different temporal ordering. In this way, possibly imprecise and/or incorrect time stamps in log files are compensated.

17 Claims, 2 Drawing Sheets

(51) Int. Cl.
  *G06N 20/00* (2019.01)
  *G06N 5/04* (2006.01)
(52) U.S. Cl.
  CPC ........... *G06F 11/0778* (2013.01); *G06N 5/04* (2013.01); *G06N 20/00* (2019.01)

(56) References Cited

U.S. PATENT DOCUMENTS

| | | | | |
|---|---|---|---|---|
| 2015/0309854 | A1* | 10/2015 | Fradkin | G06F 11/079 714/47.3 |
| 2018/0089014 | A1* | 3/2018 | Smith | H04L 43/0805 |
| 2018/0307551 | A1* | 10/2018 | Bacha | G06F 11/0709 |
| 2018/0365093 | A1* | 12/2018 | Musuvathi | G06F 11/3447 |
| 2019/0080020 | A1* | 3/2019 | Alkan | G16H 70/20 |
| 2019/0347148 | A1* | 11/2019 | Gomes Pereira | G06F 11/079 |
| 2020/0065184 | A1* | 2/2020 | Channappagoudar | G06F 11/0751 |
| 2020/0089983 | A1* | 3/2020 | Manickam | G06T 7/0012 |
| 2020/0151042 | A1* | 5/2020 | Spencer | G06N 20/00 |
| 2020/0185085 | A1* | 6/2020 | Mavrieudus | G06N 20/00 |
| 2020/0209109 | A1* | 7/2020 | Liang | G06N 3/0454 |
| 2020/0258215 | A1* | 8/2020 | Kashyap | G16H 50/20 |
| 2020/0310900 | A1* | 10/2020 | Hipp | G06Q 10/0631 |
| 2020/0344252 | A1* | 10/2020 | Menon | G06F 16/906 |
| 2021/0125684 | A1* | 4/2021 | Markowitz | G16H 10/60 |

OTHER PUBLICATIONS

Borges, Julio et al. "Predicting Target Events in Industrial Domains" Conference Paper, International Conference on Machine Learning and Data Mining in Pattern Recognition (MLDM 2017), Machine Learning and Data Mining in Pattern Recognition, pp. 17-31, Jul. 2, 2017 // https://doi.org/10.1007/978-3-319-62416-7_2.

European Search Report for European Patent Application No. 19164965.6 dated Sep. 24, 2019.

* cited by examiner

SEQUENCE MINING IN MEDICAL IOT DATA

PRIORITY STATEMENT

This application claims priority under 35 U.S.C. § 119 to European Patent Application EP 19164965.6 filed on Mar. 25, 2019 with the European Patent Office, the contents of which are herein incorporated by reference in their entirety.

FIELD

Embodiments of the invention generally relate to a a computer-implemented method for configuring a computing device for predictive maintenance, to a computer-implemented method for predictive maintenance, to a corresponding apparatus, to a corresponding computer program product, and to a corresponding data storage medium as well as to a corresponding data stream.

In particular, embodiments of the invention relate to methods and an apparatus for predictive maintenance based on medical Internet-of-Things (IoT) data. The Internet of things (IoT) is a designation for the concept of connecting a large number of devices over the Internet such that they can communicate and interact, and in particular exchange sensor data and/or control data. The term is often used in context with providing traditionally non-communication devices such as household appliances and so on with communication hardware (transceivers). The Internet of Things is one of the reasons for the large increase in available data nowadays.

BACKGROUND

In the medical domain, devices are often expensive and it is therefore of great interest to monitor the log files that such devices put out. It is therefore not unusual for medical devices to be part of an IoT-like system where the medical devices transmit their log files to a central agency or entity ("data warehouse"), there to be analyzed.

Sequence mining, or sequence pattern mining, is a discipline in which sequences of events are discovered in given data (training phase) are then (scoring phase, or inference phase) found in new data in order to trigger predictive maintenance activities. In so-called predictive maintenance, it is endeavored to predict a possible system failure before it can occur and, ideally, predicting it at a time in which preventing the failure is (still) simple and inexpensive.

In particular for very expensive machines, which are intended to be used as much as possible so as to generate sufficient value, predictive maintenance is an efficient tool to reduce downtime and thus increase efficient use of the device. For example, in medical technology, many medical imaging devices such as magnetic resonance imaging, MRI, scanners, positron emission tomography, PET, scanners, and the like are expensive and complex machines, which are desirably used to acquire images from patients during office hours of hospitals without interruption, whereas maintenance is restricted ideally to times in which no patients are present in any case.

Such medical imaging devices generate event-based log files while running. A single system typically generates every day tens thousands to hundreds of thousands lines of log data in such log files. Each line of such log files typically corresponds to an event ex, and each event ex comprises a unique identifier dx (or: unique event identifier dx) and a timestamp tx, and may optionally comprise additional data fields: ex(dx, tx, . . . ), wherein " . . . " marks the possible additional data fields.

Theoretically, based on this available data it may be possible to decide, whether a system is "healthy" or whether a system failure is imminent or likely to happen within the next x minutes, x hours, x days and/or the like. If it was known that a system failure is likely to happen, this information might be used to optimize service activities and to repair or service the system before the failure can actually happen.

One known algorithm used for searching data for meaningful sequences is the SPADE algorithm available, for example, at https://www.philippe-fournier-viger.com/spmf/SPADE.pdf.

SUMMARY

At least one embodiment of the present invention provides an improved computer-implemented method for configuring a computing device for predictive maintenance, to provide an improved computer-implemented method for predictive maintenance and to provide corresponding improved systems, computer program products, data storage media and data streams.

Advantageous options, refinements and variants are described in the claims.

Thus, according to a first embodiment, a computer-implemented method for configuring a computing device for predictive maintenance is provided, the method comprising:

providing at least one training log file comprising a list of events $e_x(d_x, t_x, \ldots)$, each training log file corresponding to at least one system, each event $e_x(d_x, t_x, \ldots)$ having at least a unique identifier $d_x$ and a timestamp $t_x$;

applying a SPADE algorithm (or a SPADE-type algorithm) to the provided at least one training log file for determining, as a configuration dataset, a sub-set comprising sequences of events $e_x(d_x, t_x, \ldots)$ which fulfills a predetermined finishing criterion $f_i$; and configuring the computing device to recognize any sequence in the configuration dataset as indicative of a system failure in an event sequence list provided to the configured computing device;

wherein within the SPADE algorithm every sub-set (or: n-tuple) of events ($e_x(d_x, t_x, \ldots)$, $e_y(d_y, t_y, \ldots)$, $e_z(d_z, t_z, \ldots)$) for the same system is considered to be a sequence, or part of a sequence, when the absolute value of $t_y-t_x$ is smaller than a predefined backward gap value, $g_b$, and when the absolute value of $t_z-t_y$ is smaller than a predefined forward gap value, $g_f$.

According to a second embodiment of the invention, a computer-implemented method for predictive maintenance is provided, comprising:

configuring a computing device (especially for predictive maintenance) using any embodiment of the method according to the first aspect so as to obtain a configured computing device;

providing at least one event sequence list (e.g. at least one inference log file) to the configured computing device (and/or receiving at least one event sequence list at the configured computing device, respectively), each event sequence list comprising a list of events $e_x(d_x, t_x, \ldots)$, and each event sequence list corresponding to at least one system, each event $e_x(d_x, t_x, \ldots)$ having at least a unique identifier $d_x$ and a timestamp $t_x$;

predicting, using the configured computing device, based on the provided at least one event sequence list whether a system failure is to be expected.

According to a third embodiment, the invention provides predictive maintenance apparatus, comprising:

an input interface for receiving at least one event sequence list (e.g. at least one finished inference log file), each event sequence list comprising a list of events $e_x(d_x, t_x, \ldots)$, and each event sequence list corresponding to at least one system, each event $e_x(d_x, t_x, \ldots)$ having at least a unique identifier $d_x$ and a timestamp $t_x$;

a computing device configured according to any embodiment of the method according to the first aspect;

wherein the configured computing device is further configured to predict, based on the provided at least one event sequence list, whether a system failure is to be expected; and wherein the predictive maintenance apparatus further comprises an output interface configured to generate a maintenance signal indicating whether (and preferably also when) a system failure is to be expected, especially of one particular system.

According to a fourth embodiment, a computer program product is provided, which comprises an executable program code, configured to, when executed, perform the method according to an embodiment of the first aspect of the invention and/or a method according to an embodiment of the second aspect of the invention.

According to a fifth embodiment, a data storage medium is provided which comprises executable program code, configured to, when executed, perform the method according to an embodiment of the first aspect of the invention and/or a method according to an embodiment of the second aspect of the invention.

According to a sixth embodiment, a data stream is provided which comprises, or is configured to generate, executable program code, configured to, when executed, perform the method according to an embodiment of the first aspect of the invention and/or a method according to an embodiment of the second aspect of the invention.

BRIEF DESCRIPTION OF THE DRAWINGS

The invention will be explained in yet greater detail with reference to example embodiments depicted in the drawings as appended.

The accompanying drawings are included to provide a further understanding of the present invention are incorporated in and constitute a part of the specification. The drawings illustrate the embodiments of the present invention and together with the description serve to illustrate the principles of the invention. Other embodiments of the present invention and many of the intended advantages of the present invention will be readily appreciated as they become better understood by reference to the following detailed description. Like reference numerals designate corresponding similar parts.

The numbering of method steps is intended to facilitate understanding and should not be construed, unless explicitly stated otherwise, to mean that the designated steps have to be performed according to the numbering of their reference signs. In particular, several or even all of the method steps may be performed simultaneously, in an overlapping way or sequentially.

Figure 1:
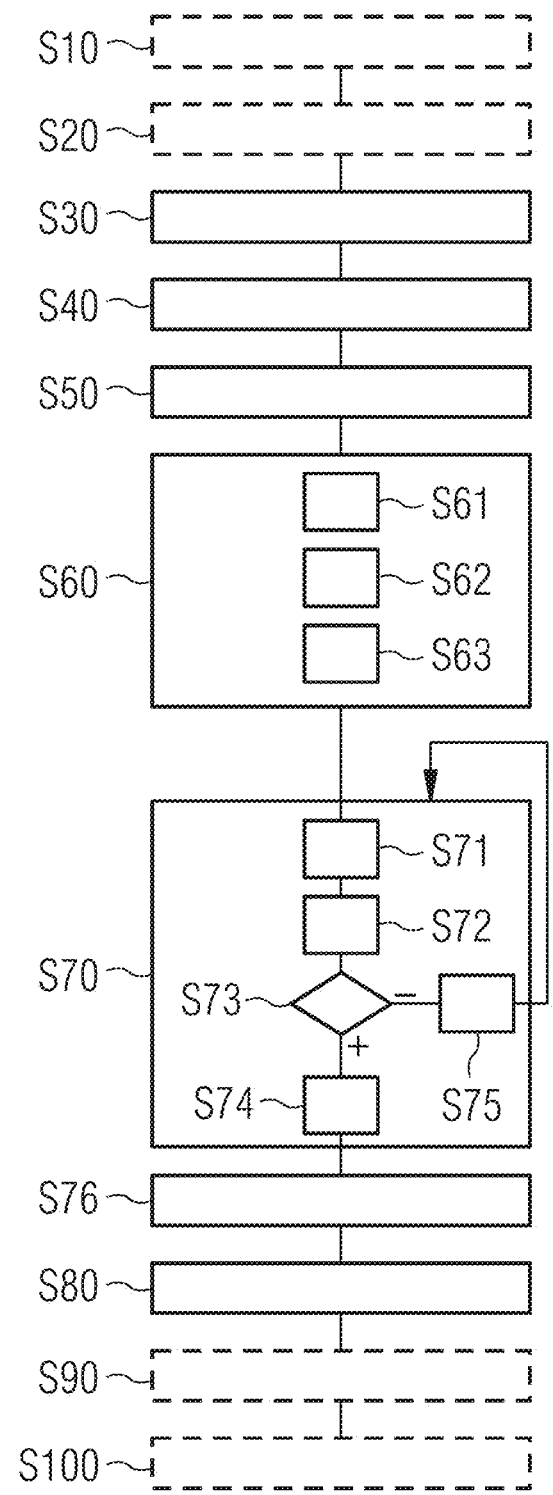
Figure 2:
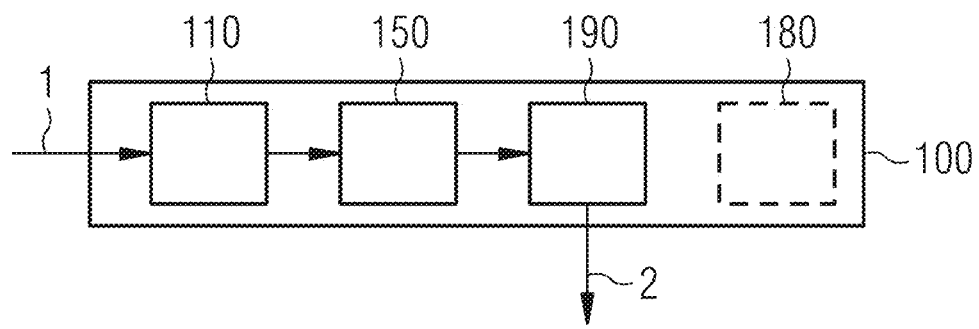
Figure 3:
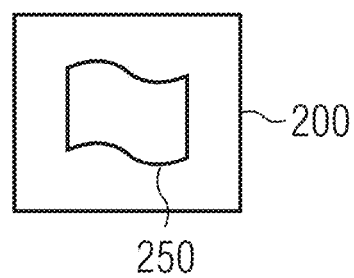
Figure 4:
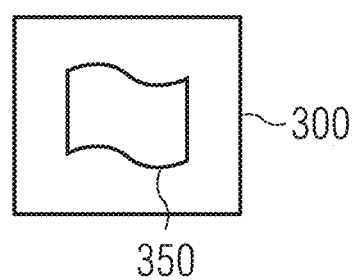

FIG. 1 shows a schematic flow diagram illustrating a method according to an embodiment of the first aspect of the present invention as well as a schematic flow diagram illustrating a method according to an embodiment of the second aspect of the present invention;

FIG. 2 shows a schematic block diagram illustrating an apparatus according to an embodiment of the second aspect of the present invention;

FIG. 3 schematically illustrates a computer program product according to an embodiment of the fourth aspect of the present invention; and FIG. 4 schematically illustrates a data storage medium according to an embodiment of the fifth aspect of the present invention.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Thus, according to a first embodiment, a computer-implemented method for configuring a computing device for predictive maintenance is provided, the method comprising:

providing at least one training log file comprising a list of events $e_x(d_x, t_x, \ldots)$, each training log file corresponding to at least one system, each event $e_x(d_x, t_x, \ldots)$ having at least a unique identifier $d_x$ and a timestamp $t_x$;

applying a SPADE algorithm (or a SPADE-type algorithm) to the provided at least one training log file for determining, as a configuration dataset, a sub-set comprising sequences of events $e_x(d_x, t_x, \ldots)$ which fulfills a predetermined finishing criterion $f_i$; and configuring the computing device to recognize any sequence in the configuration dataset as indicative of a system failure in an event sequence list provided to the configured computing device;

wherein within the SPADE algorithm every sub-set (or: n-tuple) of events $(e_x(d_x, t_x, \ldots), e_y(d_y, t_y, \ldots), e_z(d_z, t_z, \ldots))$ for the same system is considered to be a sequence, or part of a sequence, when the absolute value of $t_y-t_x$ is smaller than a predefined backward gap value, $g_b$, and when the absolute value of $t_z-t_y$ is smaller than a predefined forward gap value, $g_f$.

Thus, according to at least one embodiment of the present invention the time stamps are treated advantageously as "fuzzy" (i.e. not as strictly linearly ordered), whereas they are treated as fixedly ordered in conventional SPADE algorithms.

In other words, at least one embodiment of the present invention may be described as applying a SPADE algorithm to find a list (or: sub-set) of sequences of events which can be used as a configuration dataset indicative of a system failure while time stamps are treated as "fuzzy".

According to one particular embodiment of the first aspect, a computer-implemented method for configuring a computing device for predictive maintenance is provided, the method comprising:

providing at least one training log file comprising a list of events $e_x(d_x, t_x, \ldots)$, each training log file corresponding to at least one a system, each event $e_x(d_x, t_x, \ldots)$ having at least a unique identifier $d_x$ and a timestamp $t_x$;

labelling, in each training log file, all events within a predefined timespan and/or within a predefined number of events before any system failure of the system corresponding to the training log file occurred with preliminarily positive indicators, and all other events with preliminarily negative indicators;

providing the provided at least one training log file as input to a first iteration, i=1;

wherein the first iteration, i=1, is performed comprising:
examining all possible sequences within the input provided to the first iteration, i=1, with a sequence length $l_1=1$;

selecting, from the examined sequences, a first sub-set of sequences according to a selecting criterion $s_1$ for the first iteration, i=1, wherein the selecting criterion $s_1$ is based at least on the preliminarily positive indicators and/or the preliminarily negative indicators;

providing the selected first sub-set to at least one i-th iteration, with i>1, wherein the i-th-iteration is performed comprising:
examining all possible sequences within the input provided to the first iteration, i=1, which start with the selected (i−1)-th sub-set provided to the i-th iteration and which have a sequence length $l_i$, wherein, for all i, $l_i \geq l_{i-1}$, i.e. wherein the sequence length $l_{i+1}$ of each sequence i+1 is equal to or larger than the sequence length $l_i$ of each previous iteration i (and preferably for all i, $l_i > l_{i-1}$, i.e. wherein the sequence length $l_{i+1}$ of each sequence i+1 is strictly larger than the sequence length $l_i$ of each previous iteration i);

selecting, from the examined sequences, an i-th sub-set of sequences according to a selecting criterion $s_i$ for the i-th iteration, wherein the selecting criterion $s_i$ is based at least on the preliminarily positive indicators and/or the preliminarily negative indicators;

determining whether the selected i-th subset fulfils a finishing criterion $f_i$ for the i-th iteration, wherein, if it is determined that this is the case, the selected i-th subset is provided as a configuration dataset;

configuring the computing device to recognize any sequence in said configuration dataset as indicative of a system failure in an event sequence list (e.g. at least one inference log file) provided to the configured computing device; and providing, if it is determined that the i-th subset does not fulfil the finishing criterion $f_i$ for the i-th iteration, the selected i-th sub-set to an (i+1)-th iteration and performing the (i+1)-th iteration;

wherein, throughout this method, every sub-set (or: n-tuple) of events $(e_x(d_x, t_x, \ldots), e_y(d_y, t_y, \ldots), e_z(d_z, t_z, \ldots))$ for the same system is considered to be a sequence, or part of a sequence, when the absolute value of $t_y-t_x$ is smaller than a predefined backward gap value, $g_b$, and when the absolute value of $t_z-t_y$ is smaller than a predefined forward gap value, $g_f$ (i.e., when $|t_y-t_x|<g_b$ and $|t_z-t_y|<g_f$, with $|\ldots|$ denoting the absolute value.

The SPADE algorithm (or SPADE-type algorithm) is preferably applied such that at least two iterations are performed.

A log file corresponding to a system should be understood to mean that the log file contains, or describes, events that happened in connection with that system, preferably in/on that system. For example, the systems may comprise, or consist of, at least one medical imaging device, preferably a plurality of medical image devices. The term "a log file corresponding to a system" may therefore in some instances mean "a log file of a system" or "a log file describing a system".

The term "corresponding to at least one system" accordingly should be understood to mean that one log file may comprise events belonging to more than one system. The system to which each event belongs may be indicated by one of the fields of the event within the log file. For example, the field may comprise the serial number of the system. Such log files may be generated when one logging device generates the log file based on input from a plurality of systems.

Herein, log files that have been produced and collected in the past and for which it is known whether a system failure occurred or not and when it occurred, and which are used for configuring the computing device, are designated as "training log files", whereas log files that occur in the inference phase, i.e. that occur during the running of a system which is to be monitored using predictive maintenance are designated as event sequence list or as inference log files (in particular after they have been finalized).

In particular, an inference log file may be continuously generated and continuously provided to a configured computing device in order to predict, based on the output provided by the method according to the first aspect of the invention, whether a system failure is to be expected (and preferably, when the system is to be expected).

The computing device may be configured to implement an artificial intelligence entity.

Although the method is applicable also to only a single log file, for example a log file which comprises a plurality of system failures and the corresponding events leading up to said system failures, it is preferred that a plurality of log files is provided.

More preferably, a plurality of log files from a plurality of systems is provided, and/or a plurality of log files from a plurality of different days is provided. Most preferably, a plurality of log files from a plurality of systems and from a plurality of days is provided. The different systems in this plurality may be systems that share at least one property or application, which makes it more likely that a study of the log files of these different systems will reveal pertinent information for predictive maintenance.

Preferably, the systems to which the plurality of log files corresponds are different systems of the same type, for example, a specific type of medical imaging device, wherein the individual systems are individual devices with different serial numbers, but the same type or type number. In this way, log files may be provided that describe the health status of a plurality of devices of a particular type over a plurality of days in order to find out when that particular type of device is likely to break down based on the provided log files.

Since it is known for the training log files when systems failed in the past, the labelling is straight forward and only the predefined timespan and/or the predefined number of events has to be suitably determined, i.e. it has to be determined (or: defined) how much time, or how many events, are considered to be relevant for the sequence mining.

This may depend, for example, on the average running time of one of the systems, the average duration of one particular operation (for example, one scan of one patient) and so on. In some instances, all events corresponding to a particular system of (or: logged on) a day in which a system failure of that particular system occurred are labelled with preliminarily positive indicator values (e.g. "0"), and all events of that particular system of (or: logged on) days in which no system failure of that particular system occurred are labelled with preliminarily negative indicator values (e.g. "0"). Especially when a binary classification (e.g. "0" and "1") is used, this allows using a large amount of tools available for the treatment of such binary problems.

In the method as it is described in at least one embodiment, preferably at least two iterations are performed as it is generally expected that no single event, or in other words a sequence of length l1=1, has sufficient predictive power to predict on its own a system failure. The methods and systems described herein offer in particular advantages with respect to refining and improving each subsequent iteration so that primarily methods and systems which perform at least two iterations (that is, a first iteration i=1 and a second iteration i=2, and possibly further iterations i=3, i=4 and so on) are described to be performed.

However, it should not be understood to be excluded that a system or a method according to at least one embodiment of the present disclosure may also be configured such that in rare cases only a single iteration, i=1, is performed. In other words, a finishing criterion f1 for the first iteration i=1, may be provided, and when said finishing criterion f1 is fulfilled by the sub-set of selected sequences selected in the first iteration, i=1, then these selected sequences are provided as output, and now second iteration, i=2, is performed.

Whenever it is described herein that a criterion may comprise one or more criteria (or: one or more sub-criteria), it should be understood that the sub-criteria may be connected by logical operators such as logical AND, OR, XOR, and so on to form the criterion.

It should also be understood that a sub-set may consist of only a single sequence.

When herein "at least one i-th iteration, with i>1" is recited, this shall be understood to mean that after the first iteration, i=1, a second iteration, i=2, is performed, and possibly a third iteration, i=3, is performed, also possibly a fourth iteration, i=4, and so on. All the iterations after the first iteration, i=1, are herein for the purpose of clarity and conciseness, referred to as i-th iterations. However, this is not to be understood as there being a plurality of second iterations or something of the sort.

The terms "i-th iteration" and "(i+1)-th iteration" indicate generally the same type of iteration and are only used to describe the circumstances in which after an i-th iteration another iteration (i+1)-th iteration is performed.

The selecting criteria are preferably based on at least the preliminarily positive indicator values and/or on the preliminarily negative indicator values of the events. The preliminarily positive indicators express that the events labelled such are considered as candidate events of sequences that may predict a system failure. The preliminarily negative indicator values express that the events labelled such could be considered to be false indicators of system failure, as they have appeared also in cases where no system failure had followed.

If a certain sequence is evaluated as a candidate for predicting a system failure, occurrences of this sequence with preliminarily positive indicator values increase the likelihood that this sequence has high predictive power and occurrences of the same sequence with preliminarily negative indicator values are considered to make it less likely that the sequence has high predictive power. For simplicity, the preliminarily positive indicator values may be expressed by a "1" and the preliminarily negative indicator values by "0" (or vice versa).

Normally, in particular in conventional SPADE algorithms, a sequence of events is defined as an ordered set of events ($e_{x-1}(d_{x-1}, t_{x-1}, \ldots)$, $e_x(d_x, t_x, \ldots)$, $e_{x+1}(d_{x+1}, t_{x+1}, \ldots)$) such that $t_{x-1} < t_x < t_{x+1}$. In other words, a set of events $e_x$ is considered to be a sequence when the individual elements of that set follow on another directly in time. Such sequences are designated herein also as "temporally strict sequences". In a temporally strict sequence, herein designated by the sequence marker "=>", A=>B=>C means that B happens after A, and that C happens after B.

By contrast, in the presently described method, each timestamp $t_x$ is considered to be "fuzzy" so that a particular sequence of events ($e_{x-1}(d_{x-1}, t_{x-1}, \ldots)$, $e_x(d_x, t_x, \ldots)$, $e_{x+1}(d_{x+1}, t_{x+1}, \ldots)$) is also considered to be a sequence when $t_{x-1} < t_x < t_{x+1}$ is not necessarily true. Sequences in the sense of the present invention (which may also be designated as "fuzzy sequences") are written herein with the "fuzzy" sequence marker "~>". In yet other words, one and the same sub-set of events within a log file may be counted as multiple instances of a plurality of sequences.

For example, the sequence A=>B=>C may be present in one log file, wherein $|t_A - t_B| < g_b$, $|t_C - t_B| < g_b$, $|t_A - t_B| < g_f$ and $|t_C - t_B| < g_f$. In other words, all of the events happen very close to one another. Then, this temporally strict sequence A=>B=>C will be, according to the present invention, interpreted as the following sequences: A~>B~>C, A~>C~>B, B~>A~>C, B~>C~>A, C~>A~>B, C~>B~>A.

The reason for this is that it has been found by the inventors that, especially in IOT environments, there is a unavoidable impreciseness of timestamps due to, for example, different clocks running on different systems, time delays from the signals of the individual systems until the events signalized by the systems are logged by a logging device or logging applicant and/or the like. Therefore, it is possible that events A, B that actually happen in temporal sequence 8A->B, are erroneously logged as occurring B->A, that is, $t_B > t_A$. If, in the above example, the actual temporal sequence was B->C->A, which was logged as A=>B=>C simply because of delays and/or inaccuracies in the timestamp of the log files, then the actual temporal sequence is not present in the temporally strict sequence as it is logged, but is still present in the sequences according to at least one embodiment of the present invention.

Moreover, event log files often contain many events which are basically noise and are not relevant regarding indicating system failure, which leads to conventional sequence mining programs finding many quite similar sequences like sequence A->B->C->Noise1 and sequence A->B->C->Noise2, which just differ in some non-relevant events (Noise1, Noise2). The results may thus contain one hundred or one thousand sequences when only one meaningful sequence actually occurred, which makes evaluation and operationalization of the configured computing device (i.e. of the found model) much harder. Therefore, preferably, once all the similar sequences are found they are merged to one sequence, or a small number (preferably a number smaller than ten) using a clustering method.

In some advantageous embodiments, refinements of embodiments or variants of embodiments, the predefined backward gap value $g_b$, is smaller than the predefined forward gap value, $g_f$. Choosing a backward gap value $g_b$ different from the forward gap value $g_f$, has the advantageous effect that to some degree the actual temporal sequence of the events within the log file is considered to a certain degree since by the different gap values, a certain sense of direction in the time axis is maintained. Expressed in another way, this means that the order as logged in the log files is in general trusted to some degree. This has been found by the inventors to provide improved predictive power.

In some advantageous embodiments, refinements of embodiments or variants of embodiments, the predefined backward gap value, $g_b$, is between 0.1 seconds and 1.5 seconds, preferably between 0.7 seconds and 0.2 seconds, more preferably 1 second. In some advantageous embodiments, refinements of embodiments or variants of embodiments, the predefined forward gap value $g_f$ is between 1 second and 5 seconds, preferably between 2 seconds and 4 seconds, more preferably 3 seconds.

These values have been found by the inventors to provide an advantageous balance between gap values that produce too many sequences, i.e. too many temporarily strict sequences generating a large amount of "fuzzy sequences" (gap values too large) on the one hand and gap values which essentially only reproduce the temporarily strict sequences (gap values too small).

It will be understood that for a specific environment with specific systems, the forward and backward gap values may be adjusted, at least in part, based on properties of the individual systems, such as average, medium, minimum and/or maximum values of time differences between individual logged events.

The forward and backward gap values may also be adjusted, at least in part, based on properties of network between the systems and/or between the systems and a data warehouse for receiving the log files or for creating the log files based on data received from the systems. For example, the forward and backward gap values may be adjusted based on a latency, a delay, a difference of clocks and/or the like between the systems and/or data warehouse.

However, in systems with large time differences between individually logged events, the phenomenon of possible overlaps and/or interchanging of the actual time of events within the log file of the events will be of less relevance. Correspondingly, in systems with very small time differences between individually logged events, said phenomenon will be more important and it will in most cases not make any sense to decrease the gap values too much as they should be larger than the usual errors in the timestamps of the logged events. Taking all of these issues into consideration, the above values have been found to be optimal by the inventors.

In some advantageous embodiments, refinements of embodiments or variants of embodiments, a finishing criterion $f_i$ for all iterations consists of, or comprises, a criterion that the selected sub-sets, to be provided as output, must have a predefined target length $l_t$.

This may lead to, for example, as many iterations being performed as necessary in order to be able to output sequences of the predefined target length $l_t$. In particular, when, as it is preferred, the method is designed such that with each new iteration i the sequence length $l_i$ is increased with respect to the previous iteration i-1, in particular by 1, that a minimum number of iterations i is to be performed according to the predefined target sequence length $l_t$ (in particular until $l_i = l_t$ for at least one iteration i). In this way, it can be ensured that only actually relevant sequences are found and that the context is interpreted correctly. For example, when a sequence A->B->C->D is actually indicative of a system failure, in an earlier step the sequences:

A->B
C->D may be considered to be sequences of sequence length $l_i = 2$ indicative of system failure.

However, in the above example, when the predefined target sequence length $l_t$ is set to $l_t = 4$, the above result will be reduced to the sequence A~>B~>C~>D.

In some advantageous embodiments, refinements of embodiments or variants of embodiments, log files of a plurality of systems (preferably systems of the same device type, but with different serial number) are collected at a data warehouse (such as a local data storage device or a remote or cloud computing data storage server), and the collected log files are split, according to a predefined ratio, into training data and testing data, wherein the training data are provided as the at least one training log file for labelling and as input to the first iteration. Accordingly, the testing data may be used to test the configured computing device as to whether said configuration provides an accurate prediction of system failures.

If the results of the testing of the configured computing device are unsatisfactory, one or more hyper-parameters of the above described method may be changed. For example, one or more finishing criteria $f_i$ and/or one or more selecting criteria $s_i$ for one or more iterations i may be changed. For example, the predefined target sequence length $l_t$ may be increased or reduced, the backward gap value $g_b$ and/or the forward gap value $g_f$ may be increased and/or reduced, and/or any of the hyper-parameters of the finishing or selecting criteria $s_i$ described in the following may be adjusted.

The data warehouse may be a local device, e.g. it may be arranged at the site of a tenant (such as a hospital) to which also the systems (such as medical devices, in particular medical imaging devices) belong, wherein the data warehouse and the systems may be connected by an intranet of the tenant. The data warehouse may also be realized as a cloud service, i.e. by a cloud storage facility of a cloud computing system.

The cloud computing system may comprise a plurality of servers or processors (also known as 'cloud infrastructure'), which are geographical distributed, connected with each other via a network. A dedicated platform (herein referred to as 'cloud computing platform') is installed on the servers/processors for providing above functionality as a service (herein referred to as 'cloud service'). The cloud computing platform may comprise a plurality of software programs executed on one or more servers or processors of the cloud computing system to enable delivery of the requested service to the devices and its users.

In some advantageous embodiments, refinements of embodiments or variants of embodiments, for each of the examined sequences in each iteration a positive predictive value, PPV, score is calculated, wherein the PPV score indicates the percentage of cases in which the corresponding sequence of the examined sequences has correctly indicated a system failure compared to all cases in which the corresponding sequence of the examined sequences has indicated a system failure.

In other words, the PPV score may be defined as TP/(TP+FP), wherein TP is the amount of true predictions of system failures by said sequence and FP is the amount of false predications of system failures by said sequence. For example, one and the same sequence may in one log file appear once with a preliminarily positive indicator value (or: positive label) and once with a preliminarily negative indicator value (or: negative label). Thus, that sequence, considered as a possible indicator for a system failure, has once correctly indicated a system failure (FP=1), when it occurred once with a preliminarily positive indicator value, and would have once falsely indicated a system failure (FP=1), when it occurred with a preliminarily negative indicator value.

Thus, the PPV score of this sequence would be 1/(1+1)=½. In other words, the occurrence of said sequence in half the time correctly indicated a system failure and in the other half of the time would have falsely indicated a system failure.

The selecting criterion $s_i$ for at least one iteration i, preferably for each iteration i, preferably then consists of, or comprises, a criterion that the PPV score is larger than a predetermined threshold value $v_i$ (for a corresponding iteration i), and that a minimum number $x_i$ (for a corresponding iteration i) of examined sequences is to be selected. In any, multiple or all iterations i, the minimum number $x_i$ may be set to "1".

The predetermined threshold value $v_i$ may be the same for all iterations i. However, preferably, the predetermined threshold value $v_i$ is different for at least two different iterations i. More preferably, the predetermined threshold value $v_i$ different for all of the iterations, i.e. $v_i!=v_j$ for i!=j for all i, j.

Most preferably, the threshold value $v_i$ of each iteration i is smaller, or equal or smaller, than the threshold $v_{i+1}$ of each respective following iteration i+1. In other words, with each subsequent iteration i, the threshold value $v_i$ is either kept equal or is increased. In this way, candidate sequences are not sorted out too early, but it is ensured that eventually only the sequences with the highest predictive power, i.e. the highest PPV score, are selected as the output. Advantageously, the predetermined threshold values $v_i$ are equal to or larger than 0.5.

In preferred variants or refinements, the threshold value $v_i$ is adjusted from one iteration i to the respective next iteration i+1, especially by increasing the threshold value $v_i$.

The minimum number $x_i$ of examined sequences to be selected in each iteration may be larger than one, for example it may be one hundred, two hundred, three hundred or the like. This means that if ceteris paribus in an iteration less than $x_i$ sequences would be selected due to the selecting criterion $s_i$, instead the number $x_i$ of sequences is selected. The option of $x_i>1$ is especially advantageous when the criterion with respect to the PPV score is employed. For example, if the predefined threshold value $v_i$ for a certain iteration i is 0.7 and when the minimum number $x_i$ for said iteration i is one hundred, but only sixty of the examined sequences actually have a PPV score of 0.7 or higher, then in addition to these sixty sequences the forty sequences with the next highest PPV scores would also be selected.

Alternatively, the threshold value $v_i$ may be dynamically adjusted from iteration to iteration such that, in each iteration i, the number of examined sequences with PPV values larger (or equal to) the corresponding threshold value $v_i$ is larger than the minimum number $x_i$ of sequences to be selected for the corresponding iteration i.

Further additionally, or further alternatively, a maximum number $z_i$ of sequences to be selected for each iteration i may be defined, and the threshold value $v_i$ may be dynamically adjusted from iteration to iteration such that, in each iteration i, the number of examined sequences with PPV values larger than (or equal to) the corresponding threshold value $v_i$ is smaller than the maximum number $z_i$ of sequences to be selected. Thus, if both a minimum number $x_i$ and a maximum number $z_i$ of sequences are defined, the threshold value $v_i$ may be dynamically adjusted to keep the number of selected sequences for each iteration i in the range of from the minimum number $x_i$ to the maximum number $z_i$.

In this way, it is made sure that enough sequences are considered as candidates in a sufficient number of iterations before the output is produced. Moreover, this makes also the PPV threshold value $v_i$ "fuzzy" to a degree. The minimum number $x_i$ may be chosen in particular such that it makes optimum use of the available computing resources as it would be suboptimal to, for example, select only sixty sequences for the next iteration if enough computing power is available to examine one hundred sequences without any time loss over all.

In some advantageous embodiments, refinements of embodiments or variants of embodiments, the selecting criterion $s_i$ for all iterations i consists of, or comprises, a criterion that only such examined sequences may be selected which occur on a predefined minimum number $y_i$ of different systems according to the corresponding at least one log file. This may help to ensure that the final output is not unduly biased by the proneness of a single system (with one specific serial number) to failure after one particular sequence, which is, however, not shared by any other system. By contrast, if a selecting criterion $c_i$ at least comprises that only such examined sequences are selected which occur on the predefined minimum number $y_i$ of different systems, it is much more likely that any sequence selected has predictive power of a system failure not only for one particular individual system, but for the whole range of systems (for example, for a whole type of system).

In some advantageous embodiments, refinements of embodiments or variants of embodiments, the selecting criterion $s_i$ for at least one iteration i, preferably for all iterations i, consists of, or comprises, a criterion that only such examined sequences may be selected which occur on a predefined minimum number of different days according to the corresponding at least one training log file. This may help to ensure that external circumstances particular to a certain day do not unduly influence the eventual output.

In some advantageous embodiments, refinements of embodiments or variants of embodiments the configuration dataset is cleansed and/or partially merged using a clustering method, in particular to reduce, or eliminate, noise from the original configuration dataset as output by the final iteration of the algorithm.

According to a second embodiment of the invention, a computer-implemented method for predictive maintenance is provided, comprising:

configuring a computing device (especially for predictive maintenance) using any embodiment of the method according to the first aspect so as to obtain a configured computing device;

providing at least one event sequence list (e.g. at least one inference log file) to the configured computing device (and/or receiving at least one event sequence list at the configured computing device, respectively), each event sequence list comprising a list of events $e_x(d_x, t_x, \ldots)$, and each event sequence list corresponding to at least one system, each event $e_x(d_x, t_x, \ldots)$ having at least a unique identifier $d_x$ and a timestamp $t_x$;

predicting, using the configured computing device, based on the provided at least one event sequence list whether a system failure is to be expected.

The at least one event sequence list being provided may be a finalized list which may be also designated as an inference log file. It is preferred, however, that evince sequence lists are provide "online", or "on the fly", to the configured computing device so that event sequences that are contained within the configuration data can be determined as soon as possible.

According to a third embodiment, the invention provides predictive maintenance apparatus, comprising:

an input interface for receiving at least one event sequence list (e.g. at least one finished inference log file), each event sequence list comprising a list of events $e_x(d_x, t_x, \ldots)$, and each event sequence list corresponding to at least one system, each event $e_x(d_x, t_x, \ldots)$ having at least a unique identifier $d_x$ and a timestamp $t_x$;

a computing device configured according to any embodiment of the method according to the first aspect;

wherein the configured computing device is further configured to predict, based on the provided at least one event sequence list, whether a system failure is to be expected; and wherein the predictive maintenance apparatus further comprises an output interface configured to generate a maintenance signal indicating whether (and preferably also when) a system failure is to be expected, especially of one particular system.

The input interface may be realized as hardware, for example as a physical connector to a cable, as an antenna for receiving a wireless signal, as comprising one or more cables and so on, and/or it may be realized by software, for example comprising program code modules.

The computing device may be realised as any device, or any means, for computing, in particular for executing a software, an app, or an algorithm. For example, the computing device may comprise a central processing unit (CPU) and a memory operatively connected to the CPU. The computing device may also comprise an array of CPUs, an array of graphical processing units (GPUs), at least one application-specific integrated circuit (ASIC), at least one field-programmable gate array, or any combination of the foregoing.

Some, or even all, modules of the system may be implemented by a cloud computing platform. The computing device may be configured to realize an artificial intelligence entity.

The output interface may be realized as hardware, for example as a physical connector to a cable, as an antenna for receiving a wireless signal, as comprising one or more cables and so on, and/or it may be realized by software, for example comprising program code modules.

According to a fourth embodiment, a computer program product is provided, which comprises an executable program code, configured to, when executed, perform the method according to an embodiment of the first aspect of the invention and/or a method according to an embodiment of the second aspect of the invention.

According to a fifth embodiment, a data storage medium is provided which comprises executable program code, configured to, when executed, perform the method according to an embodiment of the first aspect of the invention and/or a method according to an embodiment of the second aspect of the invention.

According to a sixth embodiment, a data stream is provided which comprises, or is configured to generate, executable program code, configured to, when executed, perform the method according to an embodiment of the first aspect of the invention and/or a method according to an embodiment of the second aspect of the invention.

Although specific embodiments have been illustrated and described herein, it will be appreciated by those of ordinary skill in the art that the variety of alternate and/or equivalent implementations may be substituted for the specific embodiments shown and described without departing from the scope of the present invention. Generally, this application is intended to cover any adaptations or variations of the specific embodiments discussed herein.

FIG. 1 shows a schematic flow diagram illustrating a method according to an embodiment of the first aspect of the present invention.

In an optional step S10, at least one log file is collected in a data warehouse, each training log file comprising a list of events $e_x(d_x, t_x, \ldots)$, each training log file corresponding to at least one a system, each event $e_x(d_x, t_x, \ldots)$ having at least a unique identifier $d_x$ and a timestamp $t_x$.

Preferably, a plurality of log files is provided, wherein each log file corresponds to only one system. However, a plurality of log files may correspond to the same system, e.g. comprise events for one system day of one particular system each. Each event ex may have further fields, for example a field indicating an identifier (e.g. serial number) of the system to which it corresponds. Although in principle also a single log file may be used in the following case will be discussed in which a plurality of log files is provided, and in which the plurality of log files comprises a plurality of log files corresponding to a plurality of systems as well as of different days.

The data warehouse may be realized as a local device and/or as a cloud service.

In an optional step S20, the collected log files are split, according to a predefined ratio, into training data and testing data. For example, the ratio of training data:testing data may be 7:3.

In a step S30, at least one training log file is provided, each training log file comprising a list of events $e_x(d_x, t_x, \ldots)$, each training log file corresponding to at least one a system, each event $e_x(d_x, t_x, \ldots)$ having at least a unique identifier $d_x$ and a timestamp $t_x$. If step S10 and S20 have been previously performed, then advantageously the training data are provided as the at least one training log file.

In a step S40, in each training log file, all events within a predefined timespan and/or within a predefined number of events before any system failure of the system corresponding to the training log file occurred are labelled with preliminarily positive indicator values, and all other events with preliminarily negative indicator values. As has been described in the foregoing, the predefined timespan and/or predefined number of events may be defined based on properties of specific systems, or types of systems, for example on the average uptime of the involved systems, average times between failures and/or the like.

For example, a labelled training log file may have the structure as shown in the following Table 1:

TABLE 1

Example toy model training log file

| System ID | Timestamp | Event ID | Label |
|---|---|---|---|
| 1 | 01-01-2018 T08:33:49 | AX_13 | 1 |
| 1 | 01-01-2018 T08:34:13 | CCR_200 | 1 |
| 1 | ... | | |
| 2 | 01-01-2018 T06:05:12 | DB_203 | 0 |
| 2 | 01-01-2018 T06:05:12 | DB_204 | 0 |

The third line of this example log file in Table 1 describes that an event is logged which corresponds to a system No. 1 (first column), that the event is logged with a timestamp of 08:31:49 on Jan. 1, 2018 (second column), that the unique ID of that event is AX_13 (third column) and that this event is labelled with a preliminarily positive indicator value (forth column, label 1).

The second line of Table 1 indicates that, for the same system No. 1, and event CCR_200 has been logged 24 seconds after the previous event and has also been labelled with a preliminarily positive indicator value. In the last two lines of Table 1, two events, DB_203 and DB_204 are logged at the same time (6 am, five minutes and twelve seconds) for a second system 2, and have both been labelled with preliminarily negative indicator values (forth column, label "0"). Therefore, from this log file it can be inferred that at some time after the events in the second and third line of Table 1, a system failure occurred in system 1, whereas in the system No. 2, at least within the predefined time spam (or predefined number of events), no system failure of the system No. 2 has occurred.

In a step S50, the provided at least one training log file is provided as input into a first iteration i=1, of a configuration algorithm.

In a step S60, the first iteration, i=1, is performed, comprising:

In a sub-step S61, all possible sequences within the input provided to the first iteration, i=1, with a sequence length $l1=1$ are examined. For the first iteration, i=1, this simply means that all events within the input provided to the first iteration i=1 are viewed as sequences of sequence length $l1=1$.

In a sub-step S62, from the examined sequences, a first sub-set of sequences according to a selecting criterion $s_1$ for the first iteration (i=1) is selected. Preferably, the selecting criterion $s_1$ is based at least on the preliminarily positive indicator values and/or the preliminarily negative indicator values.

In the following, an example toy model is described, which serves to illustrate the method according to the first embodiment.

In this toy model, at least one training log file is provided, which comprises the following sequences according to Table 2:

TABLE 2

Example temporally strict sequences in a toy model

| Example data | Label |
|---|---|
| A => B => C => D => E => F | 1 |
| A => X => C => D => E => F | 1 |
| A => B => C => D => E => F | 0 |
| A => B => Y => D => E => F | 0 |

It should be understood that this is not necessarily a realistic example, but serves to illustrate the method as described herein. Note that A=>B=>C=>D=>E=>F means that the events A, B, C and so on have been logged with time stamps in this order but this does not necessarily mean that this is the actual order (A->B-> . . . ) in which these events actually occurred (due to latency, delays, imprecise and/or misaligned clocks and so on). In the following, it will be assumed for the sake of simplicity that the time stamps are arranged such that each of the four sequences A=> . . . in Table 2 stay the same when they are converted to "fuzzy sequences", i.e. sequences in the sense of the present invention.

However, as has been described in the foregoing, throughout this method, every sub-set (or: n-tuple) of events ($e_x(d_x, t_x, \ldots), e_y(d_y, t_y, \ldots), e_z(d_z, t_z, \ldots)$) for the same system is considered to be a sequence $e_x \sim > e_y \sim > e_z$, or part of a sequence $e_x \sim > e_y \sim > e_z$, when the absolute value of $t_y - t_x$ is smaller than a predefined backward gap value, $g_b$ (i.e. $|t_y - t_x| < g_b$), and when the absolute value of $t_z - t_y$ is smaller than a predefined forward gap value, gf (i.e. $|t_z - t_y| < g_f$). The predefined backward gap value, $g_b$, is for example 1 second, and the predefined forward gap value, $g_f$, is for example 3 seconds. Other values are possible, depending on the application at hand.

In the present example, in the first iteration, i=1, in step S62 candidate sequences of sequence length $l_1=1$ are examined, and their positive predictive value, PPV, score is calculated in each case.

The PPV score indicates the percentage of cases in which the corresponding sequence of the examined sequences has correctly indicated a system failure (value TP, "number of True Predictions") compared to all cases in which the corresponding sequence of the examined sequences has falsely indicated a system failure (value FP, "number of False Predictions"), i.e. PPV score=TP/(TP+FP).

For each of the individual candidate sequences of sequence length $l_1=1$, which are A, B, C, D, E, F, X, Y, the calculation of TP, FP and the PPV score is as follows in Table 3:

TABLE 3 candidate sequences in first iteration, i = 1

| Sequence ($l_1 = 1$) | TP | FP | PPV score TP/(TP + FP) |
|---|---|---|---|
| A | 2 | 2 | 0.50 |
| B | 1 | 2 | 0.33 |
| C | 2 | 1 | 0.66 |
| D | 2 | 2 | 0.50 |
| E | 2 | 2 | 0.50 |
| F | 2 | 2 | 0.50 |
| X | 1 | 0 | 1.00 |
| Y | 0 | 1 | 0.00 |

For example, taking the sequence consisting only of the event with event ID "A": This sequence occurs in all of the four longer sequences shown in Table 2, twice each with a preliminarily positive indicator value (label 1) and with a preliminarily negative indicator value (label 0). This means that the sequence "A", if considered as a candidate for indicating a system failure, would have truly predicted a system failure in two cases (TP=2; first two lines of Table 2) and would have falsely predicted a system failure in two cases (FP=2; last two lines in Table 2). Accordingly, the PPV score for the sequence "A" in the first iteration i=1 indicated by Table 3 is 0.50. Similarly, the PPV score is for all the other examined sequences of sequence length l1=1 (or: candidate sequences) is calculated and shown in the fourth column of Table 3.

In this toy model, the selecting criterion s1 for the first iteration i=1 shall comprise, or consist of, the criterion that the PPV score for an examined sequence to be selected must be larger than 0.50. As is evident from Table 3, this is only true for the examined sequences of length l1=1 with the event IDs "C" and "X".

As has been described in the foregoing, the selecting criterion s1 may comprise further criteria, preferably all connected with logical AND operators.

It shall be assumed that the selecting criterion $s_1$ for the first iteration, i=1, resulted in that a sub-set consisting of the two sequences of length 1 ($l_1$=1) with the event IDs "C" and "X" is selected.

Then, in a step S63, the selected sequences ("C", "X") are provided, as a sub-set, to at least one further, i-th, iteration, in this case, to a second iteration, i=2, in the next step. As has been described, in some variants already in the first iteration, i=1, a finishing criterion as described in the following may be applied.

If, for the sake of the toy model, it is assumed that no finishing criterion $f_1$ for the first iteration i=1 is set, then these selected sequences "C", "X" are now provided S63 as a sub-set to the second iteration, i=2.

In a step S70, the second iteration, i=2, is performed, comprising the following sub-steps:

In a step S71, all possible sequences within the input provided to the 1st iteration which start with the sequences selected in the (i−1)-th iteration (here: in the $1^{st}$ iteration, i=1) and which have a sequence length $l_i$ are examined (or: put together). Preferably, for all i, $l_i \geq l_{i-1}$, and more preferably, for all i, $l_i \geq l_{i-1}$, i.e. the length of the sequences examined in each iteration i can only increase with respect to previous iterations j with j<i. More preferably, as will be described also for the present toy model, the length of the sequences examined increases by 1 with each iteration, i.e. $l_i = l_{i-1} + 1$.

In the present example, $l_2$ is set to 2 ($l_2$=2) such that, in the second iteration, i=2, all possible sequences of the original input to the first sequence, i=1, are examined which have a length of 2 and which start with either "C" or "X" (the sub-set provided by the first iteration, i=1, to the second iteration, i=2), see first column of Table 4 in the following.

In a step S72, from the examined sequences, an i-th sub-set of sequences is selected according to a selecting criterion $s_2$ for the 2nd iteration, i=2, (or, accordingly, for any i-th iteration, according to a selecting criterion $s_i$), wherein the selecting criterion $s_2$ is based at least on the preliminarily positive indicator values and/or the preliminarily negative indicator values.

The same calculations as for Table 3 are now performed for the second iteration, i=2, as shown in excerpts in the following Table 4. PPV scores of sequences that do not occur are labelled as "NA", short for "Not Available". Of course, these may also be labelled in any other way, for example by a PPV score of zero, making sure that these are never selected (either as output or as input for a potential next iteration).

TABLE 4 some candidate sequences in second iteration, i = 2

| Sequence (sequence length $l_2 = 2$) | TP f | FP | PPV score TP/(TP + FP) |
|---|---|---|---|
| C~>A | 0 | 0 | NA |
| C~>B | 0 | 0 | NA |
| C~>C | 0 | 0 | NA |
| C~>D | 2 | 1 | 0.66 |
| C~>E | 0 | 0 | NA |
| C~>F | 0 | 0 | NA |
| C~>X | 0 | 0 | NA |
| C~>Y | 0 | 0 | NA |
| . . . | | | |
| X~>A | 0 | 0 | NA |
| X~>B | 0 | 0 | NA |
| X~>C | 1 | 0 | 1.00 |
| . . . | | | |

It can be seen that in this toy model, at the second iteration, i=2, the sequence X~>C is considered to be the sequence with the highest predictive power, followed by the sequence C~>D (PPV score 0.66). This is because, if one examines Table 2, the occurrence of X=>C always leads, according to the at least one log file, to a system failure (label 1), whereas the occurrence of sequence C=>D at least in two thirds of occurrences leads, according to the at least one log file, to a system failure.

In this example, starting with the second iteration, i=2, in a step S73 it is determined whether the selected i-th subset fulfils a finishing criterion $f_i$ for the i-th iteration (here: $f_2$ for the second iteration i=2), wherein, if it is determined that this is the case (denoted by a "+" in FIG. 1), the selected i-th subset is provided in a step S74 as a configuration dataset, i.e. as an output of the algorithm. Thus, the configuration dataset has been determined using a SPADE algorithm (or SPADE-type algorithm).

If it is determined that the i-th subset does not fulfil (denoted by a "−" in FIG. 1) the finishing criterion $f_i$ for the i-th iteration (here: $f_2$ for the second iteration i=2), the selected i-th subset is provided, in a step S75, to an (i+1)-th iteration (here: third iteration, i=3, for example with l3=3) and the algorithm continues at step S70 for performing the (i+1)-th iteration (here: third iteration, i=3).

For example, the finishing criterion $f_i$ may comprise the criterion that the selected sub-set must have sequences of a minimum target sequence length $l_{t,min}$. The fact that in this example there is no finishing criterion for the first iteration i=1 may thus also be described in that there is a finishing criterion $f_1$ but that the finishing criterion $f_i$ for all iterations i comprises the criterion that the minimum target sequence length $l_{t,min}$=2. Of course, the finishing criterion $f_i$ may also comprise, or consist of, the criterion that the selected sub-set must have sequences of exactly an exact target sequence length $l_{t,ex}$.

When, in step S74, the output of the algorithm is provided eventually (assuming that in some—then final—iteration the according finishing criterion $f_i$ is met), in an optional step S76, all similar sequences are merged to one sequence, or a small number (preferably a number smaller than ten) of sequences using a clustering method, eliminating noise. The result of step S76 is used in the following as an updated configuration dataset instead of the configuration dataset originally output by step S75, if the optional step S76 is performed.

In a step S80, a computing device is configured to recognize sequences in the configuration dataset (or, in other words, any of the sequences in said configuration dataset) as indicative of a system failure in an event sequence list (e.g. an inference log file) to be provided to the configured computing device during an inference phase (or: inference stage). As mentioned above, the configuration dataset used for configuring the computing device may be the original configuration dataset or a dataset generated from the original configuration dataset by the cleansing and/or partially merging performed in step S76.

It will be understood that the description of this toy model is not intended to be limiting, but only serves to provide a better understanding of the ideas, options and variants described herein. Moreover, it should be understood that although the method according to FIG. 1 has been described using an illustrative toy model, the method is in no way restricted to that.

The method may further comprise the following steps (in which case the method may also be designated as a computer-implemented method for predictive maintenance according to the second embodiment of the present invention):

In a step S90, at least one event sequence list (e.g. at least one inference log file) is provided to the configured computing device, each event sequence list comprising a list of events $e_x(d_x, t_x, \ldots)$, and each event sequence list corresponding to a system, each event $e_x(d_x, t_x, \ldots)$ having at least a unique identifier $d_x$ and a timestamp $t_x$. Preferably, the event sequence lists are of the same shape as the training log files.

In a step S100, using the configured computing device, based on the provided at least one event sequence list it is predicted whether a system failure is to be expected. Each event sequence list may be used to predict S100 whether a system failure is to be expected in any of the at least one system to which the event sequence list corresponds.

Preferably, the computing device scans each event sequence list for any of the at least one sequence in the configuration dataset provided of the above-described algorithm and determines, if any of them are present, that a system failure for a particular system (that is one of the at least one systems to which that event sequence list) is to be expected.

Optionally, it may also be predicted in step S100 when the system failure is to be expected, e.g. based on the duration between the first and the last event in a sequence that has been found in the event sequence list and which equals one of the sequences in the configuration dataset.

FIG. 2 shows a schematic block diagram for illustrating a predictive maintenance apparatus 100 according to an embodiment of the third aspect of the present invention.

The predictive maintenance apparatus 100 comprises an input interface 110 for receiving at least one event sequence list 1 (e.g. at least one inference log file), each event sequence list 1 comprising a list of events $e_x(d_x, t_x, \ldots)$, and each event sequence list 1 corresponding to at least one system, each event $e_x(d_x, t_x, \ldots)$ having at least a unique identifier $d_x$ and a timestamp $t_x$.

The predictive maintenance apparatus 100 further comprises a computing device 150 configured according to the method according to an embodiment of the first aspect, for example as has been described with respect to FIG. 1 in the foregoing. The computing device 150 is further configured to predict, based on the provided at least one event sequence list 1, whether a system failure is to be expected, especially by scanning the at least one event sequence list 1 for any of the sequences in the configuration dataset.

The predictive maintenance apparatus 100 also comprises an output interface 190 configured to generate a maintenance signal 2 indicating whether a system failure is to be expected. The maintenance signal 2 may control a display (e.g. an optional display 180 of the predictive maintenance apparatus 100) to display a warning relating to the expected failure, control a sound output unit to output an acoustic warning signal and/or the like. The maintenance signal 2 may control other steps in a workflow, for example cause a maintenance to be scheduled for the system expected to fail, it may cause at least one function of the system expected to fail to be re-scheduled and/or to be re-tasked to a different system (for example, if the system is a medical imaging device, a scan scheduled for a patient may be re-scheduled for a time after the automatically scheduled maintenance, or it may be re-tasked to a different medical imaging device within the same hospital) and/or the like.

FIG. 3 schematically illustrates a computer program product 200 according to an embodiment of the fourth aspect of the present invention. The computer program product 200 comprises an executable program code 250, configured to, when executed, perform the method according to an embodiment of the first aspect of the invention and/or a method according to an embodiment of the second aspect of the invention, for example as has been described with respect to FIG. 1 in the foregoing.

FIG. 4 schematically illustrates a data storage medium 300 according to an embodiment of the fifth aspect of the present invention. The data storage medium 300 comprises an executable program code 350, configured to, when executed, perform the method according to an embodiment of the first aspect of the invention and/or a method according to an embodiment of the second aspect of the invention, for example as has been described with respect to FIG. 1 in the foregoing.

In the foregoing detailed description, various features are grouped together in one or more examples or examples with the purpose of streamlining the disclosure. It is to be understood that the above description is intended to be illustrative, and not restrictive. It is intended to cover all alternatives, modifications and equivalents. Many other examples will be apparent to one skilled in the art upon reviewing the above specification.

The embodiments were chosen and described in order to best explain the principles of the invention and its practical applications, to thereby enable others skilled in the art to best utilize the invention and various embodiments with various modifications as are suited to the particular use contemplated. In the appended claims and throughout the specification, the terms "including" and "in which" are used as the plain-English equivalents of the respective terms "comprising" and "wherein," respectively. Furthermore, "a" or "one" does not exclude a plurality in the present case.

It is one of the ideas of the present invention that training log files comprising event sequences are examined iteratively for sequences of increasing length in order to determine a set of configuration data containing event sequences that have high predictive power for a system failure. Forward and backward gap values are defined such that not only sequences in the exact same temporal order as in the training log files are examined but also sequences with slightly different temporal ordering. In this way, possibly imprecise and/or incorrect time stamps in log files are compensated.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for maintenance of a medical imaging device, the method comprising:
   providing at least one training log file including a list of events, each of the at least one training log file corresponding to at least one medical imaging device, and each event in the list of events including at least a unique identifier and a timestamp;
   applying a SPADE algorithm to the at least one training log file to determine, as a configuration dataset, a sub-set including sequences of events that fulfill a finishing criterion;
   configuring a computing device to recognize a sequence of events, in the configuration dataset as indicative of a failure of the medical imaging device, in an event sequence list provided to the computing device;
   providing at least a first event sequence list to the computing device, the first event sequence list including a first list of events, and the first event sequence list corresponding to the medical imaging device;
   predicting, using the computing device, a failure of the medical imaging device based on the first event sequence list; and
   at least one of (i) automatically scheduling maintenance of the medical imaging device or (ii) rescheduling or re-tasking at least one function of the medical imaging device, in response to predicting the failure of the medical imaging device, wherein
      the re-tasking re-tasks the at least one function of the medical imaging device to a different medical imaging device, and
      within the SPADE algorithm, each sub-set of events for a same medical imaging device is considered to be a sequence, or part of a sequence, when an absolute value of a difference between a first event timestamp and a second event timestamp, of the sequence of events, is less than a defined backward gap value, and when an absolute value of a difference between a third event timestamp and the first event timestamp, of the sequence of events, is less than a defined forward gap value.

2. The method of claim 1, wherein the applying a SPADE algorithm comprises:
   labelling, in each respective training log file of the at least one training log file, (i) all events within at least one of a defined timespan and a defined number of events before any system failure of the medical imaging device corresponding to the respective training log file occurred with preliminarily positive indicators, and (ii) all other events with preliminarily negative indicators, and
   providing the at least one training log file as input to a first iteration, i=1;
   wherein the first iteration, i=1, includes
      examining sequences within the input provided to the first iteration, i=1, with a first sequence length l1=1,
      selecting, from the sequences, a first sub-set of sequences according to a first selecting criterion for the first iteration, i=1, wherein the first selecting criterion is based at least on at least one of the preliminarily positive indicators or the preliminarily negative indicators, and
      providing the first sub-set of sequences to an i-th iteration, with i>1, and
   wherein the i-th-iteration includes
      examining possible sequences starting with an (i−1)-th sub-set of sequences, which is provided to the i-th iteration, with a sequence length li, wherein for all i, li≤li−1,
      selecting, from the possible sequences, an i-th sub-set of possible sequences according to an i-th selecting criterion for the i-th iteration, wherein the i-th selecting criterion is based at least on at least one of the preliminarily positive indicators or the preliminarily negative indicators,
      determining whether the i-th subset fulfils a finishing criterion for the i-th iteration,
      providing the i-th subset as a configuration dataset in response to determining that the i-th subset fulfils the finishing criterion for the i-th iteration; and
      providing the i-th subset to an (i+1)-th iteration and performing the (i+1)-th iteration in response to determining indicating that the i-th subset does not fulfil the finishing criterion for the i-th iteration.

3. The method of claim 1, wherein the defined backward gap value is less than the defined forward gap value.

4. The method of claim 3, wherein at least one of
the defined backward gap value is between 0.1 seconds and 1.5 seconds, or
the defined forward gap value is between 1 second and 5 seconds.

5. The method of claim 2, wherein finishing criterion of all iterations includes a criterion that subsets selected to be provided as the configuration dataset, must have a defined target sequence length.

6. The method of claim 2, wherein log files of a plurality of medical imaging devices are collected at a data warehouse, and wherein the log files collected are split, according to a defined ratio, into training data and testing data, and wherein the training data are provided as the at least one training log file for the labelling and as input into the first iteration.

7. The method of claim 2, further comprising:
calculating, for each of the sequences examined in each iteration, a positive predictive value (PPV) score, the PPV score indicating a percentage of cases in which a corresponding sequence of events has correctly indicated a system failure; and
the i-th selecting criterion includes a criterion that the PPV score is greater than a threshold value for each iteration and that a minimum number of examined sequences is to be selected for each iteration i.

8. The method of claim 7, wherein the threshold value is adjusted from the i-th iteration to an (i+1)-th iteration.

9. The method of claim 8, wherein the threshold value of the i-th iteration is less than or equal to the threshold value of the (i+1)-th iteration.

10. The method of claim 7, wherein the minimum number of examined sequences to be selected for each iteration is less than or equal to a minimum number for the (i+1)-th iteration.

11. The method of claim 2, wherein the i-th selecting criterion includes a criterion that only examined sequences, which occur on a defined minimum number of different medical imaging devices according to a corresponding at least one training log file, are selectable.

12. The method of claim 2, wherein the i-th selecting criterion includes a criterion that only examined sequences, which occur on a defined minimum number of different days according to a corresponding at least one training log file, are selectable.

13. The method of claim 1, wherein the configuration dataset is at least one of cleansed or partially merged using a clustering method.

14. A predictive maintenance apparatus, comprising:
an input interface configured to receive at least one event sequence list, each at least one event sequence list including a list of events, and each at least one event sequence list corresponding to at least one medical imaging device, each event of the list of events including at least a unique identifier and a timestamp;
a computing device configured according to the method of claim 1;
and
an output interface configured to generate a maintenance signal indicating the predicted failure of the medical imaging device.

15. A computer program product including a non-transitory computer-readable medium storing instructions that, when executed by a predictive maintenance apparatus or a computing device, cause the predictive maintenance apparatus or the computing device to carry out the method of claim 1.

16. A non-transitory computer readable medium storing a computer program including instructions that, when executed by a predictive maintenance apparatus or a computing device, cause the predictive maintenance apparatus or the computing device to carry out the method of claim 1.

17. A non-transitory computer readable medium storing a computer program including instructions that, when executed by a predictive maintenance apparatus or a computing device, cause the predictive maintenance apparatus or the computing device to carryout the method of claim 3.

* * * * *